(12) United States Patent
Choi

(10) Patent No.: US 11,675,846 B2
(45) Date of Patent: Jun. 13, 2023

(54) NUTRITIONAL BALANCE PROVIDING SYSTEM BASED ON PET HEALTH INFORMATION

(71) Applicant: allfin Inc., Yongin-si (KR)

(72) Inventor: Sang Ho Choi, Gimpo-si (KR)

(73) Assignee: allfin Inc., Yongin-si (KR)

( * ) Notice: Subject to any disclaimer, the term of this patent is extended or adjusted under 35 U.S.C. 154(b) by 0 days.

(21) Appl. No.: 16/566,722

(22) Filed: Sep. 10, 2019

(65) Prior Publication Data
US 2021/0073294 A1 Mar. 11, 2021

(51) Int. Cl.
*G06F 16/903* (2019.01)
*G06F 16/9038* (2019.01)

(52) U.S. Cl.
CPC .... *G06F 16/90335* (2019.01); *G06F 16/9038* (2019.01)

(58) Field of Classification Search
None
See application file for complete search history.

(56) References Cited

U.S. PATENT DOCUMENTS

| 2009/0148560 A1* | 6/2009 | Shiba | A23K 20/163 |
| | | | 426/61 |
| 2014/0141134 A1* | 5/2014 | Johnson | A23K 40/00 |
| | | | 426/231 |
| 2016/0073659 A1* | 3/2016 | Zemel | A23K 50/42 |
| | | | 426/2 |
| 2016/0253742 A1* | 9/2016 | Bosher | G06Q 30/06 |
| | | | 705/26.82 |
| 2018/0064140 A1* | 3/2018 | Li | A23K 10/16 |
| 2021/0065277 A1* | 3/2021 | Bramson | A01K 11/006 |

FOREIGN PATENT DOCUMENTS

| KR | 101746397 B1 * | 2/2017 | G01N 1/38 |
| KR | 20170156953 A * | 11/2017 | G06Q 30/02 |
| KR | 2018113744 A * | 10/2018 | A01K 29/005 |

OTHER PUBLICATIONS

Chapter 5 Macronutrients from Small Animal Clinical Nutrition, Hand et al., Small Animal Clinical Nutrition, 5th Edition, Published by Mark Morris Associates, Published 2010. (Year: 2010).*

* cited by examiner

*Primary Examiner* — Kris E Mackes
*Assistant Examiner* — Soheila (Gina) Davanlou
(74) *Attorney, Agent, or Firm* — Studebaker & Brackett PC

(57) ABSTRACT

The present invention relates to a system for providing nutritional balance based on pet health information, and more particularly, to a system for providing nutritional balance based on pet health information, which determines the amount of supply of a recipe in consideration of pet information, such as the kind, a growth stage, and an activity stage of a pet, and the amount of motion of a pet obtained from a sensor attached to a pet, thereby providing an optimum recipe and amount.

9 Claims, 20 Drawing Sheets

Fig. 3

| Sample | Hg | As | Cd | Pb | Al | Ba |
|---|---|---|---|---|---|---|
| | 1-2 | 0.2-2 | 0.1-0.3 | 2-4 | 10-20 | 2-3 |
| BANGSILI_190212 | 0.137 | 0.035 | 0.020 | 0.127 | 8.584 | 0.759 |
| BANGSILI_190507 | 0.063 | 0.063 | 0.030 | 0.179 | 11.433 | 0.526 |

| Sample | U | Bi | Ni | Ca | Mg | Na |
|---|---|---|---|---|---|---|
| | 0.5-2 | 0.5-2 | 1-2 | 300-1200 | 25-120 | 40-300 |
| BANGSILI_190212 | 0.003 | 0.059 | 0.258 | 182.326 | 44.157 | 363.220 |
| BANGSILI_190507 | 0.004 | 0.096 | 0.192 | 187.353 | 62.208 | 180.273 |

Fig. 5

| ITEM | AMOUNT OF NUTRIENT REQUIREMENTS | REQUIREMENT AMOUNT LIMIT (AMOUNT OF REQUIREMENT %) | | AMOUNT OF NUTRIENT SUPPLY |
|---|---|---|---|---|
| | | MINIMUM | MAXIMUM | |
| MOISTURE CONTENT (%) | 50 | 100 | 110 | 50 |
| FEED FEEDING AMOUNT (g) | | | | 265.8 |
| AMOUNT OF DRY MATTER INTAKE (g) | 136 | * | * | 131.8 |
| PROTEIN (g), DRY MATTER | 24.40 | 120 | 200 | 26 |
| TRYPTOPHAN (g), DRY MATTER | 0.22 | 120 | 200 | 0.23 |
| CALCIUM (g), DRY MATTER | 0.68 | 130 | 150 | 1.00 |
| PHOSPHORUS (g), DRY MATTER | 0.54 | 130 | 150 | 0.74 |
| FAT (g), DRY MATTER | 7.40 | 120 | 300 | 22 |

Fig. 6

| ITEM | AMOUNT OF NUTRIENT REQUIREMENTS | REQUIREMENT AMOUNT LIMIT (AMOUNT OF REQUIREMENT %) | | AMOUNT OF NUTRIENT SUPPLY |
|---|---|---|---|---|
| | | MINIMUM | MAXIMUM | |
| LINOLEIC ACID(g), DRY MATTER | 1.52 | 120 | 200 | 2.60 |
| LINOLENIC ACID(g), DRY MATTER | 0.05 | 120 | 200 | 0.00 |
| VITAMIN A(RE), DRY MATTER | 203.34 | 120 | 200 | 402.65 |
| SODIUM(g), DRY MATTER | 0.11 | 120 | 500 | 0.42 |
| POTASSIUM(g), DRY MATTER | 0.81 | 120 | 200 | 0.86 |
| TOTAL DIETARY FIBER(g), DRY MATTER | 0.00 | 120 | 200 | 0.00 |
| INSOLUBLE DIETARY FIBER(g), DRY MATTER | 0.00 | 120 | 200 | 0.00 |
| WATER-SOLUBLE DIETARY FIBER(g), DRY MATTER | 0.00 | 120 | 200 | 0.00 |

Fig. 7

| | | | |
|---|---|---|---|
| DESEXUALIZED ADULT DOG | 112 | AMOUNT OF ENERGY CONSUMPTION IN REST STATE | 70 |
| GENERAL ADULT DOG | 126 | DESEXUALIZED ADULT CAT | 84 |
| OVERWEIGHT OR FAT DOG | 98 | GENERAL CAT | 98 |
| LOW INTENSIVELY ACTING SPECIAL DOG | 140 | OVERWEIGHT OR FAT CAT | 70 |
| NORMAL ACTING SPECIAL DOG | 210 | ACTIVE CAT | 112 |
| HIGH INTENSIVELY ACTING SPECIAL DOG | 280 | | |
| ACTIVE AND YOUNG ADULT DOG | 140 | NEWFOUNDLAND DOG | 105 |
| ACTIVE GREAT DANE | 200 | OLD AND ACTIVE ADULT DOG | 105 |
| ACTIVE TERRIER | 180 | | |
| INACTIVE ADULT DOG | 95 | | |

Fig. 8A

| MAJOR CLASSIFICATION | MIDDLE CLASSIFICATION | MINOR CLASSIFICATION | RAW MATERIAL PRICE (Won/Kg) | MIXING AMOUNT (g) PER HEAD DAILY | MIXING AMOUNT (g) 1 SERVING | MIXING RATIO (%) |
|---|---|---|---|---|---|---|
| | | TOTAL | - | 26.6 | 20.0 | 100.00 |
| STOCKBREEDING PRODUCT | EGG YOLK | EGG YOLK POWDER | 21,000 | 33.96 | 25.48 | 127.40 |
| STOCKBREEDING PRODUCT | EGGSHELL | EGGSHELL POWDER | 7,700 | 1.46 | 1.10 | 0.55 |
| AGRICULTURAL PRODUCT | SHIITAKE MUSHROOM | SHIITAKE MUSHROOM POWDER | 22,000 | 0.00 | 0.00 | 0.00 |
| MARINE PRODUCT | GREEN LAVER | GREEN LAVER POWDER | 28,400 | 0.00 | 0.00 | 0.00 |
| AGRICULTURAL PRODUCT | SWEET POTATO | SWEET POTATO POWDER | 16,500 | 34.69 | 26.07 | 130.35 |
| STOCKBREEDING PRODUCT | CHICKEN BREAST | CHICKEN BREAST POWDER | 52,000 | 0.00 | 0.00 | 0.00 |
| MARINE PRODUCT | ANCHOVY | ANCHOVY POWDER | 31,000 | 14.29 | 10.71 | 53.56 |

Fig. 8B

| RAW MATERIAL USE LIMIT (%) | | PRICE (Won/Kg) | | DISCOUNT PRICE (Won/Kg) | DRY MATTER (%) | MOISTURE (%) |
|---|---|---|---|---|---|---|
| MINIMUM | MAXIMUM | ORIGINAL MATTER | WIND DRY MATTER | | | |
| * | * | 10231 | 18155 | * | * | * |
| 0.00 | 100.0 | 2674 | | | 85.88 | 14.11 |
| 0.00 | 100.0 | 47 | | | 88.00 | 12.00 |
| 0.00 | 0.20 | 0 | | | 89.21 | 10.81 |
| 0.00 | 10.0 | 0 | | | 84.34 | 15.35 |
| 0.00 | 100.0 | 215 | | | 87.75 | 12.25 |
| 0.00 | 100.0 | 0 | | | 87.45 | 12.50 |
| 0.00 | 100.0 | 1380 | | | 85.88 | 16.91 |
| ⋮ | | | | | | |

Fig. 9A

| MAJOR CLASSIFICATION | MIDDLE CLASSIFICATION | MINOR CLASSIFICATION | RAW MATERIAL PRICE (Won/Kg) | MIXING AMOUNT (g) | | MIXING RATIO (%) |
|---|---|---|---|---|---|---|
| | | | | PER HEAD DAILY | 1 SERVING | |
| AGRICULTURAL PRODUCT | BROCCOLI | BROCCOLI POWDER | 36,500 | 0.00 | 0.0 | 0.00 |
| AGRICULTURAL PRODUCT | CABBAGE | CABBAGE POWDER | 25,300 | 3.09 | 2.28 | 1.14 |
| AGRICULTURAL PRODUCT | PERILLA | PERILLA POWDER | 45,667 | 0.00 | 0.0 | 0.00 |
| AGRICULTURAL PRODUCT | BOILED RICE | INSTANT RICE | 4,500 | 135.59 | 90.0 | 45.00 |
| OTHERS | OTHERS | TRYPTOPHAN | 493,333 | 0.07 | 0.05 | 0.03 |
| OTHERS | OTHERS | CHOLINE | 656,333 | 0.00 | 0.00 | 0.00 |
| OTHERS | OTHERS | VITAMIN-MINERAL PREMIX | 4,700 | 0.41 | 0.31 | 0.15 |
| OTHERS | OTHERS | WATER | 0 | 59.07 | 44.0 | 22.00 |

Fig. 9B

| RAW MATERIAL USE LIMIT (%) | | PRICE (Won/Kg) | | DISCOUNT PRICE (Won/Kg) | DRY MATTER (%) | MOISTURE (%) |
|---|---|---|---|---|---|---|
| MINIMUM | MAXIMUM | ORIGINAL MATTER | WIND DRY MATTER | | | |
|  | 100.0 | 0 |  |  | 98.1 | 1.9 |
|  | 100.0 | 28 |  |  | 92.0 | 3.0 |
|  | 100.0 | 0 |  |  | 82.1 | 17.9 |
| 20.0 | 80.0 | 20 |  |  | 98.8 | 81.2 |
|  | 100.0 | 13 |  |  | 100.0 |  |
|  | 100.0 | 0 |  |  | 100.0 |  |
|  | 100.0 | 7 |  |  | 100.0 |  |
|  | 100.0 | 0 |  |  | 0.0 | 100.0 |

| MINOR CLASSIFICATION | RAW MATERIAL PRICE (Won/Kg) | PROTEIN (%) | TRYPTOPHAN (%) | CALCIUM (%) | PHOSPHORUS (%) | FAT (%) |
|---|---|---|---|---|---|---|
| TOTAL | * | * | * | * | * | * |
| EGG YOLK POWDER | 21,000 | 30.87 | | 0.20 | 0.89 | 54.80 |
| EGGSHELL POWDER | 7,000 | 2.57 | | 35.78 | 0.09 | 0.89 |
| SHIITAKE MUSHROOM POWDER | 24,000 | 18.59 | 0.28 | 0.05 | 0.58 | 3.72 |
| GREEN LAVER POWDER | 35,000 | 16.74 | 0.24 | 0.32 | 0.10 | 4.47 |
| SWEET POTATO POWDER | 16,000 | 4.00 | 0.04 | 0.03 | 0.07 | 2.53 |
| CHICKEN BREAST POWDER | 52,000 | 88.31 | 0.51 | 0.03 | 0.53 | 7.28 |
| ANCHOVY POWDER | 31,000 | 68.00 | 0.24 | 2.89 | 2.15 | 13.11 |

Fig.10B

| LINOLEIC ACID (%) | LINOLENIC ACID (%) | ASH (%) | VITAMIN A (RE/100g) | CARBOHYDRATE (%) | CRUDE FIBER (%) | SODIUM (%) | POTASSIUM (%) |
|---|---|---|---|---|---|---|---|
| * | * | * | * | * | | * | * |
| | | | | | | | |
| | | | | | | | |
| | | | | | | | |
| | | | | | | | |
| | | | | | | | |
| | | | | | | | |

| MINOR CLASSIFICATION | RAW MATERIAL PRICE (Won/Kg) | PROTEIN (%) | TRYPTOPHAN (%) | CALCIUM (%) | PHOSPHORUS (%) | FAT (%) |
|---|---|---|---|---|---|---|
| BROCCOLI POWDER | | | | | | |
| CABBAGE POWDER | | | | | | |
| PERILLA POWDER | | | | | | |
| INSTANT RICE | | | | | | |
| TRYPTOPHAN | | | | | | |
| CHOLINE | | | | | | |
| VITAMIN-MINERAL PREMIX | | | | | | |
| WATER | | | | | | |

Fig. 11B

| LINOLEIC ACID (%) | LINOLENIC ACID (%) | ASH (%) | VITAMIN A (RE/100g) | CARBOHYDRATE (%) | CRUDE FIBER (%) | SODIUM (%) | POTASSIUM (%) |
|---|---|---|---|---|---|---|---|
| 2.33 | | 10.57 | | | 12.5 | 0.10 | 3.92 |
| | | 9.26 | | | 10.55 | 0.04 | 2.83 |
| | | 1.34 | | | 1.00 | 0.04 | 0.80 |
| | | 1.04 | | | 0.80 | 0.03 | 0.90 |
| | | | | | | | |
| | | | 0.700.00 | | | | |
| | | | | 4.00 | 8.00 | | |

⋮

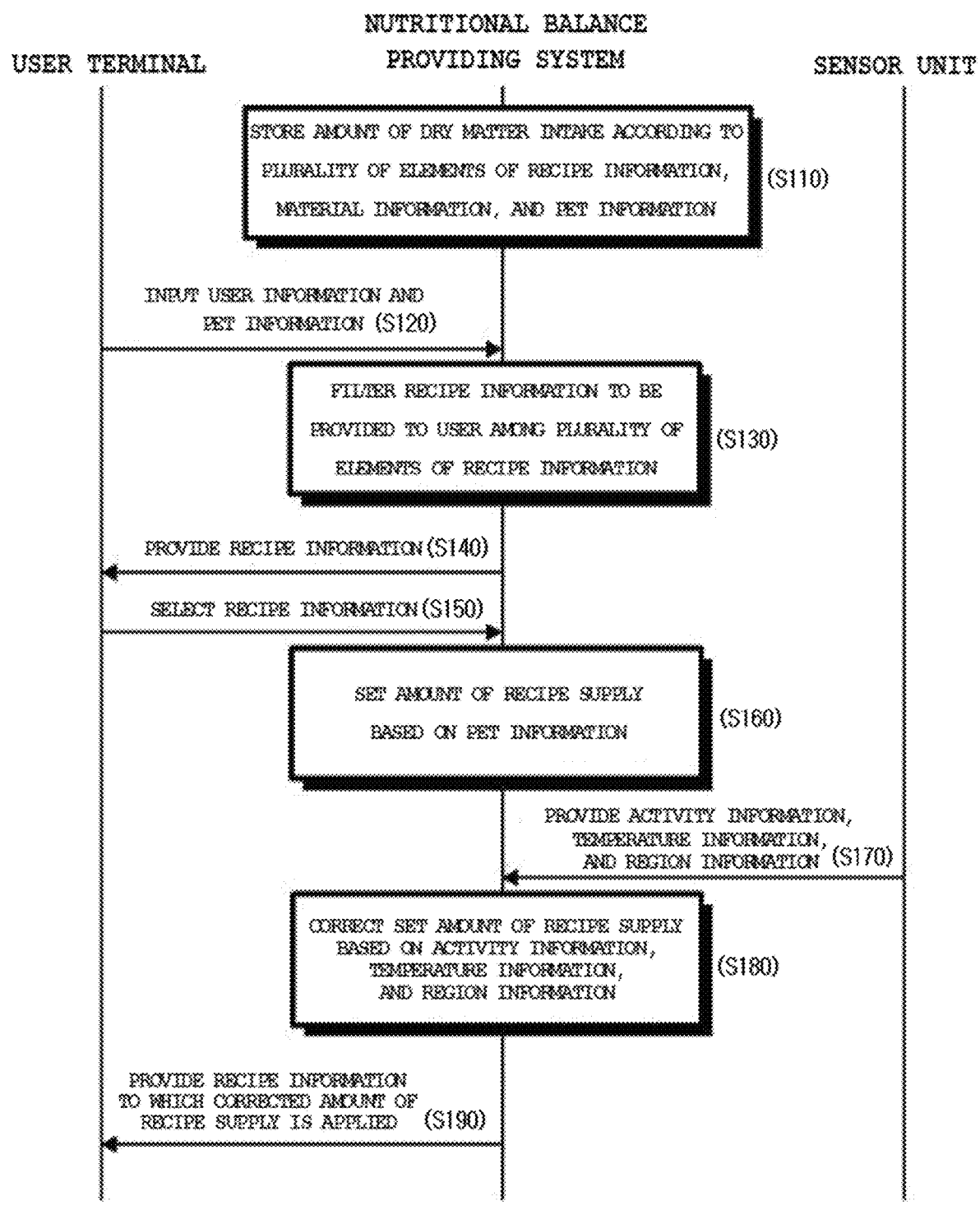

NUTRITIONAL BALANCE PROVIDING SYSTEM BASED ON PET HEALTH INFORMATION

TECHNICAL FIELD

The present invention relates to a system for optimizing nutritional balance based on pet health information and providing information, and more particularly, to a system for providing nutritional balance based on pet health information, which determines the amount of supply of a recipe in consideration of pet information, such as the kind, a growth stage, and an activity stage of a pet, and the amount of motion of a pet obtained from a sensor attached to a pet, a hair health diagnosis kit of a pet, an intestine health diagnosis kit of a pet, a blood test of a pet, and the like, thereby providing an optimum recipe and amount.

BACKGROUND ART

Due to the rapid economic growth and the improvement of the national income level, the number of households raising pets increases rapidly in Korea and at present, the population raising pets reaches as many as 5 million, and the number of pets also increases by 100,000 to 200,000 every year. It is predicted that the number of households raising pets will continuously increase in the future, and according to this trend, the pet industry, such as animal hospitals, goods, and feed related to pets, has been developed, and is expected to continuously grow.

In the past, people raised pets to have fun, but recently, people consider pets not just as animals, but as family members and companions of life, and strive to provide a better environment and provide good food for pets.

In the meantime, there are many cases where many people raising pets provide their pets with their food. However, since there are many possibilities in that food made for people to eat is high calorie food or is imbalanced in nutritive ingredients, and contains ingredients that pet should not eat, the food may not be suitable to pets for eating. In actuality, pets have many diseases by eating food that humans eat.

Even when many people raising pets provide food in consideration of the kinds and the states of their pets, it is realistically difficult to make food in consideration of all of various elements for pets, and there is a problem in that it is difficult to accurately determine the amount of food provided for pets.

SUMMARY OF THE INVENTION

The present invention has been made in an effort to provide a system for providing nutritional balance based on pet health information, which determines the amount of supply of a recipe in consideration of pet information, such as the kind, a growth stage, and an activity stage of a pet, and the amount of motion of a pet obtained from a sensor attached to a pet, thereby providing an optimum recipe and amount.

An exemplary embodiment of the present invention provides a system for providing nutritional balance based on pet health information, the system including: an information input unit configured to receive pet information from a user terminal; and a recipe providing unit configured to provide the user terminal with a plurality of elements of recipe information pre-stored in a storage unit, and receive a selection of one or more elements of the recipe information among the plurality of elements of recipe information from the user terminal, in which the recipe providing unit determines the amount of recipe supply included in the one or more selected elements of recipe information based on the input pet information. In the exemplary embodiment, the pet information may include any one or more among the kind, a breed, growth and activity stages, current weight, target weight, age, a medical history, pregnancy, spaying or neutering, and evasive material information of a pet.

In the exemplary embodiment, the storage unit may store any one or more among the plurality of elements of the recipe information, material information included in the plurality of elements of the recipe information, and the amount of requirements of nutrients and the amount of dry matter intake according to the pet information.

In the exemplary embodiment, the material information may include any one or more among an origin of a material, classification, a raw material price, a mixing amount, a mixing ratio, a raw material use limit, the amount of dry matters, the amount of moisture, the amount of protein, the amount of fat, the amount of carbohydrate, the amount of tryptophan, the amount of calcium, the amount of phosphorus, the amount of linoleic acid, the amount of ash, the amount of vitamin, the amount of crude fiber, the amount of dietary fiber, the amount of sodium, and the amount of potassium.

In the exemplary embodiment, the recipe providing unit may calculate the amount of intake requirements of the dry matter according to the pet information based on Equation 1 below.

$$\text{Amount of intake requirements of dry matter} = \frac{\left(\begin{array}{c}\text{Amount of intake requirements}\\ \text{of dry matter according to}\\ \text{growth and activity stages} \times \\ \text{target weight}^{0.75}\end{array}\right) \times 1000}{(\text{Feed energy})} \quad <\text{Equation 1}>$$

In the exemplary embodiment, the recipe providing unit may determine the amount of recipe supply based on Equation 2 below.

$$\text{Amount of recipe supply} = \frac{\left(\begin{array}{c}\text{Amount of intake requirements}\\ \text{of dry matter} \times \text{feed energy}\end{array}\right)}{\text{Recipe energy}} \quad <\text{Equation 2}>$$

In the exemplary embodiment, the system may further include a sensor unit, which is attached to a body of a pet, and obtains any one or more among activity information, temperature information, and region information from the pet, in which the recipe providing unit may correct the amount of recipe supply based on any one or more among the activity information, the temperature information, and the region information.

In the exemplary embodiment, the recipe providing unit may exclude recipe information including the evasive material information among the plurality of elements of recipe information based on the evasive material information and provide the user terminal with the recipe information.

In the exemplary embodiment, the information input unit may receive an input of user information from the user terminal, and the storage unit may match the user information and the recipe information selected from the user terminal that inputs the user information and store the matched information.

In the exemplary embodiment, the recipe providing unit may provide the user terminal that inputs the user information with recommended recipe information based on the matched and stored user information and recipe information.

The present invention has an effect in that it is possible to provide an optimum recipe and amount and alleviate an already occurring disease by determining the amount of supply of a recipe in consideration of pet information, such as the kind, a growth stage, and an activity stage of a pet, and the amount of motion of a pet obtained from a sensor attached to a pet, diagnosis information through a diagnosis kit, and the like.

The present invention has an effect in that it is possible to prevent a disease in a pet due to an evasive material by setting a material which the pet should avoid based on pet information and excluding a recipe including the set evasive material.

BRIEF DESCRIPTION OF THE DRAWINGS

FIGS. 3 and 4 are diagrams illustrating examples of examination information through diagnosis kits for pet.

FIGS. 5 to 11B are diagrams schematically illustrating data stored in a storage unit 120 in the system 100 for providing nutritional balance based on pet health information according to the exemplary embodiment of the present invention.

FIG. 16 is a flowchart for describing a series of processes for providing a recipe for a pet by using the system 100 for providing nutritional balance based on pet health information according to the exemplary embodiment of the present invention.

DETAILED DESCRIPTION

Hereinafter, an exemplary embodiment is presented for helping understanding of the present invention. However, the exemplary embodiment below is simply provided for easier understanding of the present invention, and the contents of the present invention are not limited by the exemplary embodiment.

Figure 1:
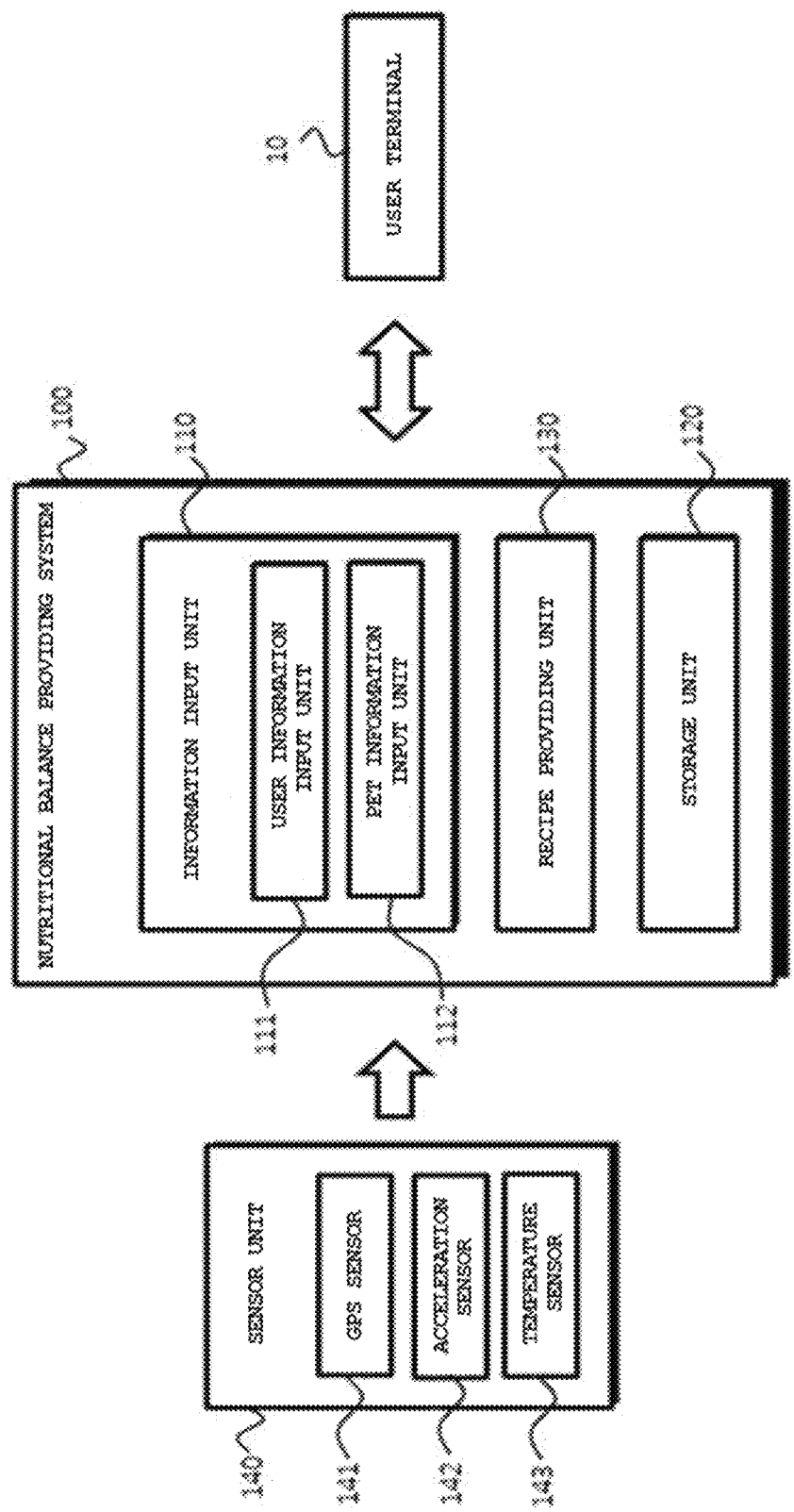
FIG. 1 is a diagram schematically illustrating constituent elements of a system 100 for providing nutritional balance based on pet health information according to an exemplary embodiment of the present invention.
Figure 2:
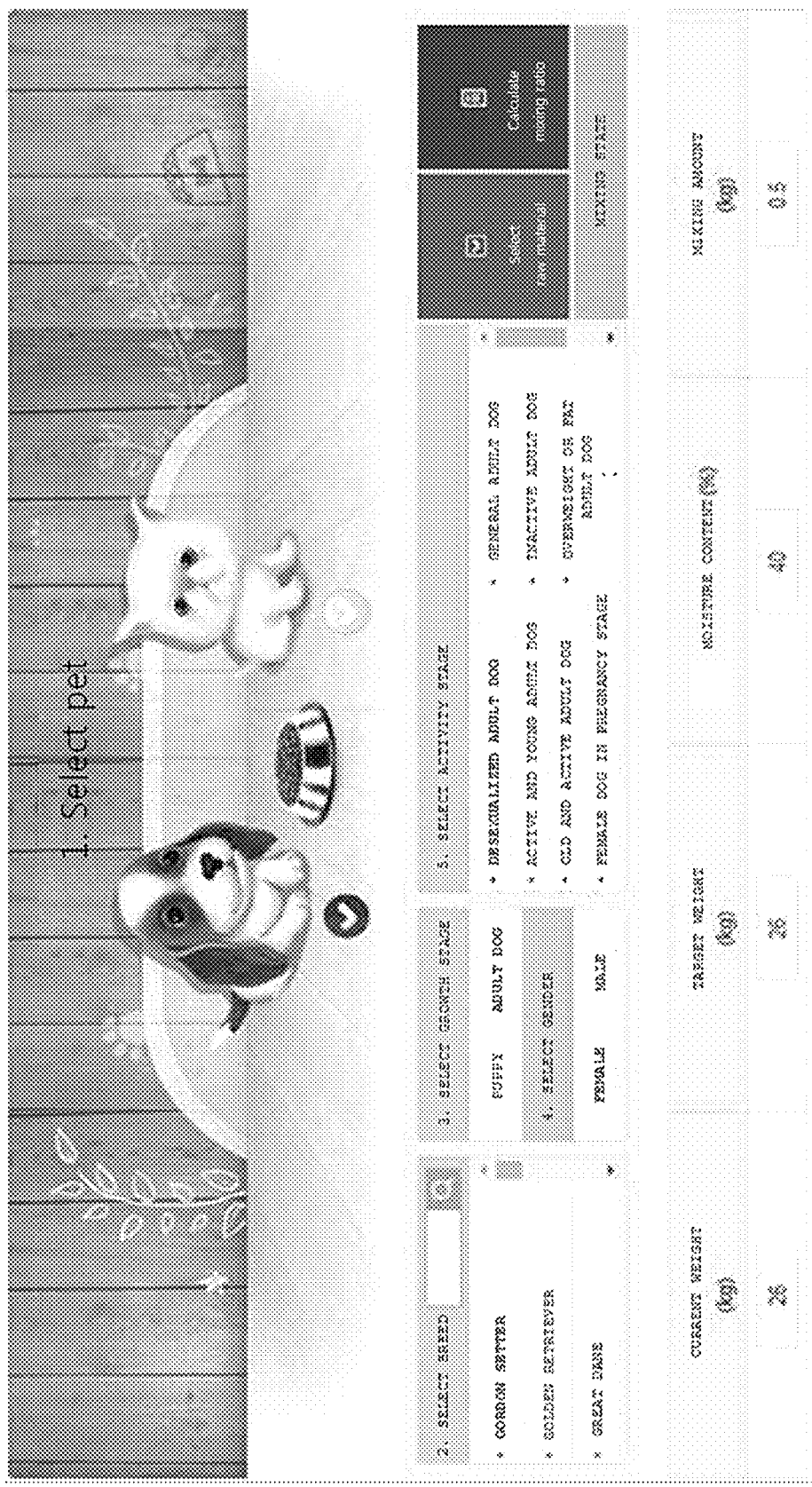
FIG. 2 is a diagram schematically illustrating an interface provided to a user terminal 10 in order for an information input unit 110 to receive an input of pet information from a user in the system 100 for providing nutritional balance based on pet health information according to the exemplary embodiment of the present invention.

FIG. 1 is a diagram schematically illustrating constituent elements of a system 100 for providing nutritional balance based on pet health information according to an exemplary embodiment of the present invention, FIG. 2 is a diagram schematically illustrating an interface provided to a user terminal 10 in order for an information input unit 110 to receive an input of pet information from a user in the system 100 for providing nutritional balance based on pet health information according to the exemplary embodiment of the present invention, FIGS. 5 to 11B are diagrams schematically illustrating data stored in a storage unit 120 in the system 100 for providing nutritional balance based on pet health information according to the exemplary embodiment of the present invention, and FIGS. 12 to 15 are diagrams schematically illustrating an interface, in which recipe information is output to the user terminal 10 when the user terminal 10 is a smart phone, in the system 100 for providing nutritional balance based on pet health information according to the exemplary embodiment of the present invention.

Referring to FIGS. 1 to 4, the system 100 for providing nutritional balance based on pet health information according to the exemplary embodiment of the present invention may include an information input unit 110, a storage unit 120, and a recipe providing unit 130.

Herein, the system 100 for providing nutritional balance based on pet health information illustrated in FIGS. 1 to 4 is the exemplary embodiment, and the constituent elements thereof are not limited to the exemplary embodiment illustrated in FIGS. 1 to 4, and may be added, changed, or deleted as necessary. For example, in a system 100' for providing nutritional balance based on pet health information according to another exemplary embodiment of the present invention, the information input unit 110, the storage unit 120, and the recipe providing unit 130 are not formed as separate constituent elements, but are formed as one recipe providing server (not illustrated) to perform all of the roles of the three constituent elements.

First, the information input unit 110 may receive user information and pet information from a user terminal 10. To this end, the information input unit 110 may include a user information input unit 111 and a pet information input unit 112.

Herein, the user terminal 10 may include any one or more among a mobile communication terminal, a Personal Digital Assistant (PDA), a laptop, a smart phone, a netbook computer, a Mobile Internet Device (MID), an Ultra Mobile Personal Computer (UMPC), and a tablet PC used by a user. For example, when the user terminal 10 is a smart phone, the user terminal 10 is connected with the system 100 for providing nutritional balance based on pet health information according to the exemplary embodiment of the present invention through an application installed in the smart phone to use a pet recipe providing service provided by the system 100 for providing nutritional balance based on pet health information.

Herein, the user information is the information for identifying a user using the system 100 for providing nutritional balance based on pet health information according to the exemplary embodiment of the present invention. For example, the user information may include any one or more among a name, an age, a gender, and an address, and the user information may be the information input in a process of joining a membership in order for a user to use the pet recipe providing service provided by the system 100 for providing nutritional balance based on pet health information.

Herein, the pet information may be the information required for identifying a pet and determining a state of the pet. For example, the pet information may include any one or more among the kind, a breed, growth and activity stages, current weight, target weight, an age, a medical history, pregnancy, spaying or neutering, evasive material information of a pet.

The pet information may include examination information about blood, hair, enterobacteria, genes, and the like obtainable through examinations performed on pets, or include diagnosis information of a diagnosis kit used for pets.

Herein, a hair diagnosis kit for obtaining hair examination information for pet may be used, and the corresponding kit collects and analyzes hairs of an animal to recognize nutrition information (including Hg, As, Cd, Pb, Al, Ba, U, Bi, Ni, Ca, Mg, Na, K, Cu, Zn, P, Fe, Mn, Cr, and Se) of the hair.

Referring to FIG. 3, a nutritional balance of a recipe may be adjusted through the diagnosis information obtained through the hair diagnosis kit. FIG. 3 represents an example of a pet of which a level of Na is measured to be higher than a normal level, and as a result of the supply of the feed for three weeks with decreased contents of protein, potassium, and calcium of the recipe according to this information, it was observed that the high liver index and the high cholesterol level were decreased and the level of Na was also decreased to be normal.

A beneficial intestinal bacteria diagnosis kit for obtaining enterobacteria examination information for a pet may be used, and the corresponding kit collects and analyzes samples in the intestine to recognize a level for the enterobacteria (including tobacillus, clostridium, blautia, enterococcus, firmicutes, bacteroidetes, and the like).

Figure 4:
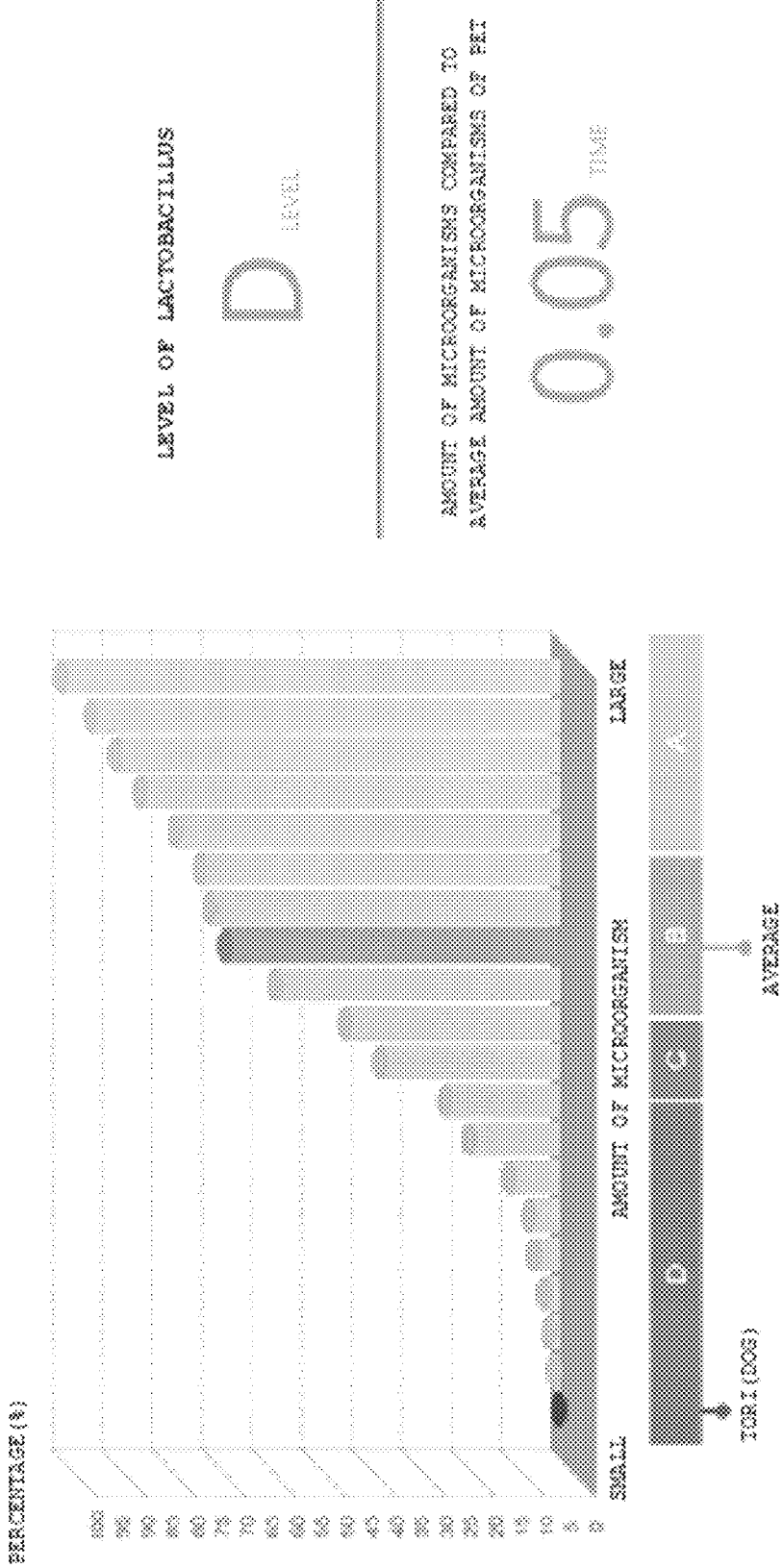

Referring to FIG. 4, it is possible to recommend an appropriate lactobacillus product through the diagnosis information obtained through the beneficial intestinal bacteria diagnosis kit.

The information input unit 110 provides the user terminal 10 with an interface, through which pet information is inputtable, as illustrated in FIG. 2, thereby inducing the user to input pet information.

In one exemplary embodiment, the information input unit 110 may input pet information by receiving a selection of one or more elements of information among the plurality of elements of pre-stored pet information. For example, the information input unit 110 may subdivide the growth and activity stages of the pet into a desexualized adult dog, a general adult dog, an overweight or fat dog, a low intensively acting special dog, a normally acting special dog, a high intensively acting special dog, an active and young adult dog, an active and Great Dane, an active terrier, an inactive adult dog, a Newfoundland dog, and an old and active adult dog, and pre-store the subdivided growth and activity stages, and may receive a selection of any one or more among the stored growth and activity stages of the pet from the user to receive an input of the growth and activity stages of the pet. However, the present invention is not limited thereto.

The storage unit 120 may store any one or more among the plurality of elements of recipe information, information on materials included in the plurality of elements of recipe information, and the amount of nutrient requirements and a dry matter intake according to the pet information.

Figure 13:
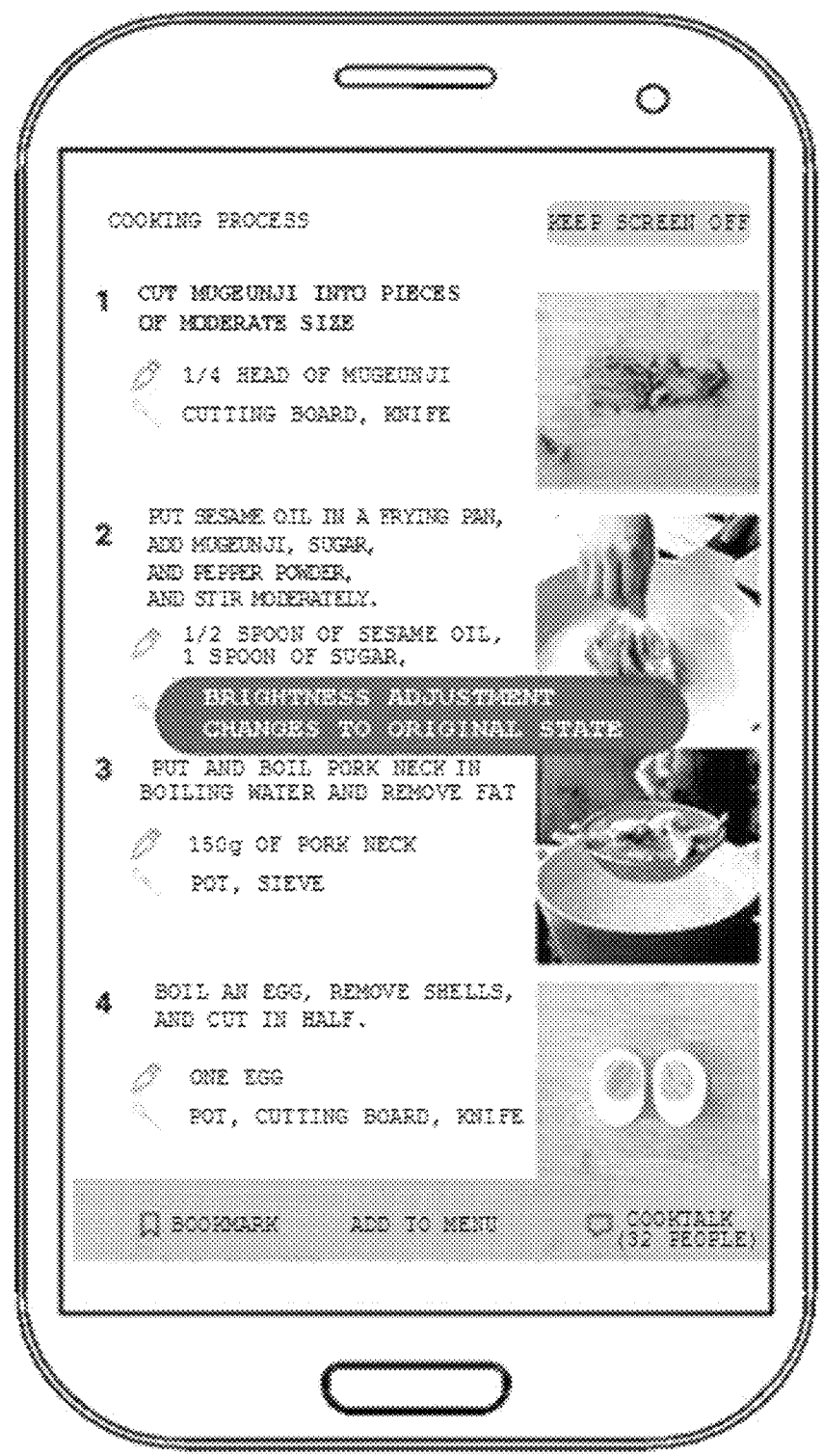
Figure 14:
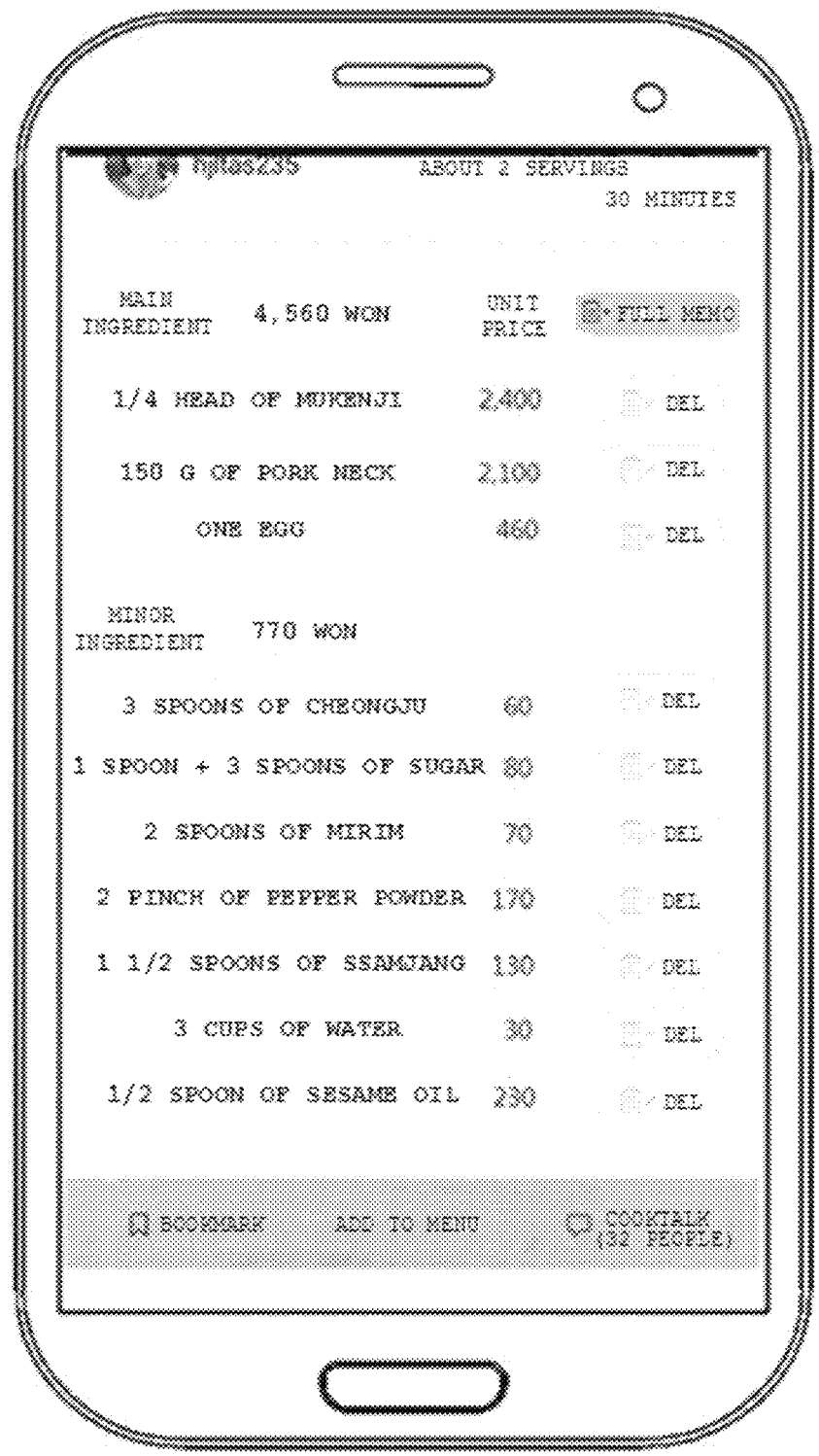
Figure 15:
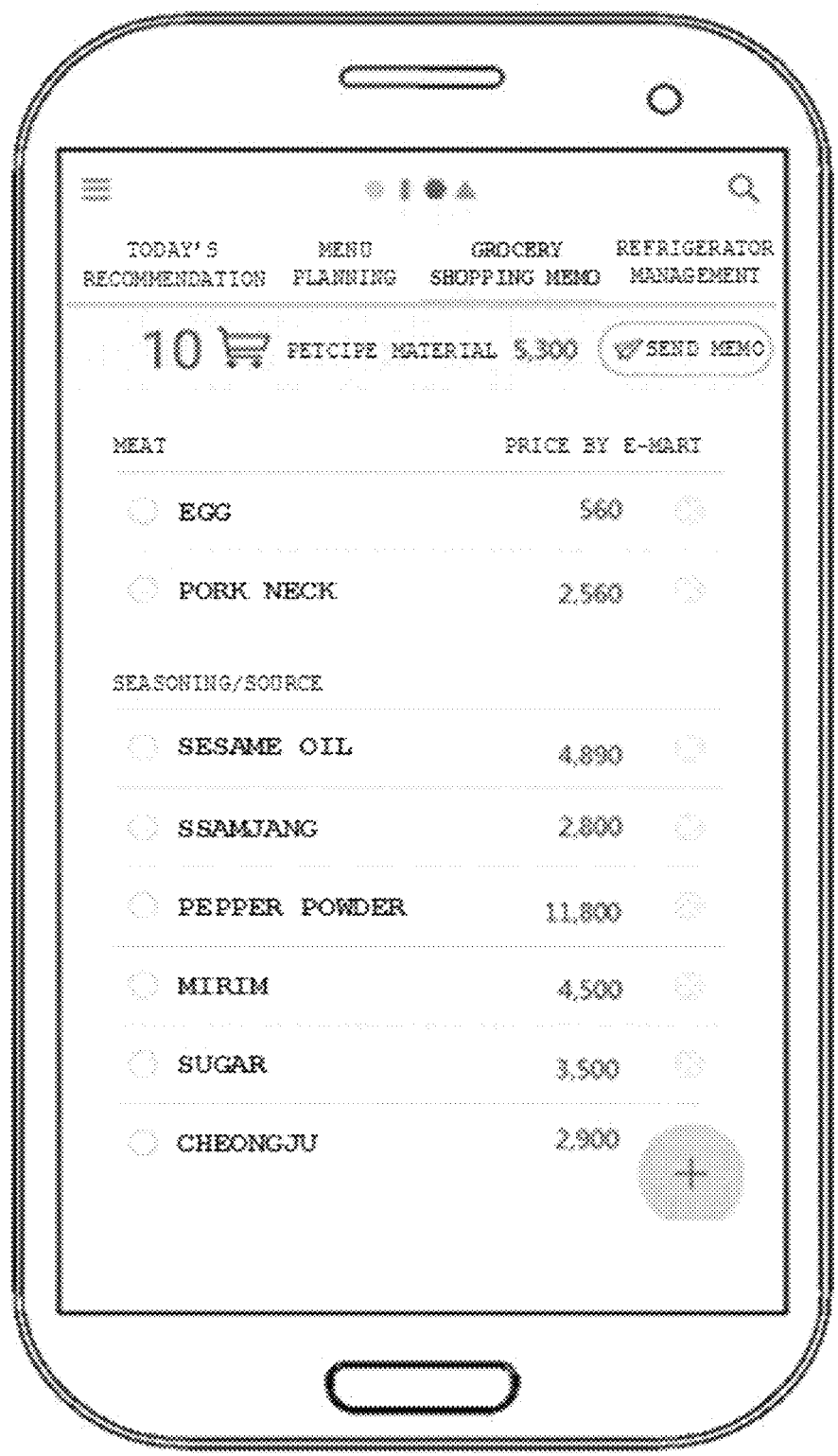

Herein, the recipe information is the information about a method of making food to be provided to a pet. For example, as illustrated in FIGS. 13 to 15, the recipe information may include material information, information on a unit price of a material, and food cooking sequence information.

Herein, the material information is the information about materials included in food and a nutritive component included in the material. For example, the material information may include any one or more among an origin of a material, classification, a raw material price, a mixing amount, a mixing ratio, a raw material use limit, the amount of dry matters, the amount of moisture, the amount of protein, the amount of fat, the amount of carbohydrate, the amount of tryptophan, the amount of calcium, the amount of phosphorus, the amount of linoleic acid, the amount of ash, the amount of vitamin, the amount of crude fiber, the amount of dietary fiber, the amount of sodium, and the amount of potassium, as illustrated in FIGS. 5 to 7.

The storage unit 120 may store any one or more among the kinds of agricultural, stockbreeding, and marine products, an origin, a form of an original matter, a form of a dry matter, and a cooking type. For example, the storage unit 120 may generally divide the material information into an agricultural product, a stockbreeding product, a marine product, a by-product, and others, and store information about the stockbreeding products (89 kinds including chicken, pork, beef, and the like), the marine products (26 kinds including anchovy and pollack, the agricultural products (133 kinds including rice, sweet potato, potato, and the like), the by-products (56 kinds including a liver and a lung of a pig, and the like), and three other kinds for each classification. In this case, the storage unit 120 may exclude all of the food materials known to be harmful to pets, and may carefully select and store raw materials based on materials that have been used or may be used for pets at home and abroad.

The storage unit 120 may store the amount of dry matters taken according to the growth and activity stages in the pet information as illustrated in FIGS. 8A to 11B.

The storage unit 120 may receive the plurality of elements of recipe information, the material information included in the plurality of elements of recipe information, the amount of nutrient requirements and the amount of dry matters intake according to the pet information from an external server and store the received information, and may make the received information in the form of a data table and store the data table. To this end, the storage unit 120 may include one or more databases (DBs).

In the exemplary embodiment, the storage unit 120 may match the user information input from the user terminal 10 and the recipe information selected from the user terminal 10 which inputs the user information and store the matched information. Through this, the user may check a history of the recipe information selected by the user.

In the exemplary embodiment, the storage unit 120 may store user recipe information input from the user terminal 10. Herein, the user recipe information may mean the material information directly input by the user, the information on a unit price of a material, and food cooking sequence information. For example, when the user desires to share his/her recipe with other people, the user may input the user recipe information through the information input unit 110, and the storage unit 120 may store the input user recipe information. When a request for providing the user recipe information is input from other user terminals 10 later, the user recipe information may be provided through the recipe providing unit 130 which is to be described later. However, the present invention is not limited thereto.

Figure 12:
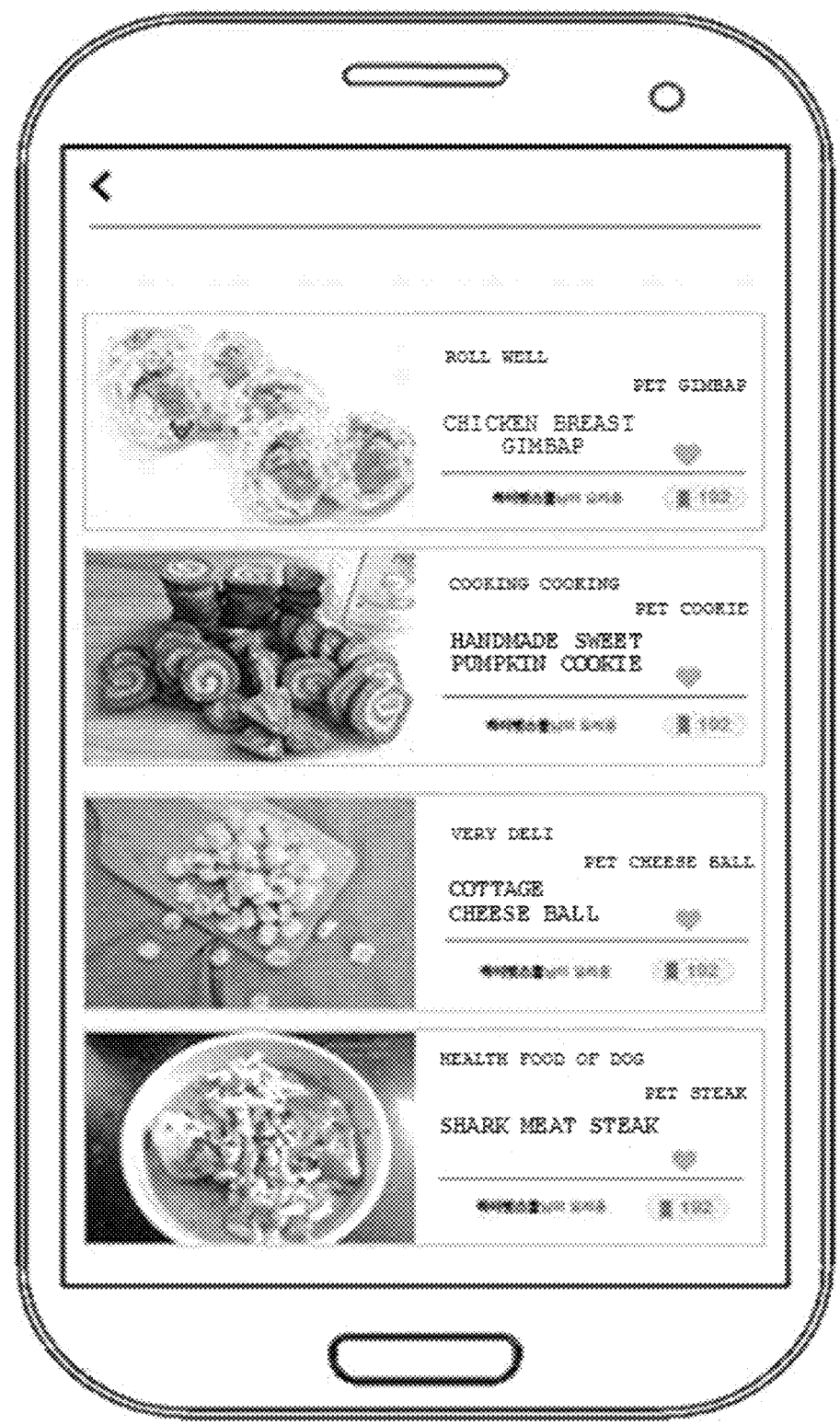
FIGS. 12 to 15 are diagrams schematically illustrating an interface, in which recipe information is output to the user terminal 10 when the user terminal 10 is a smart phone, in the system 100 for providing nutritional balance based on pet health information according to the exemplary embodiment of the present invention.

The recipe providing unit 130 may provide the user terminal 10 with the plurality of elements of the recipe information pre-stored in the storage unit 120 as illustrated in FIG. 12 and receive a selection of one or more elements of recipe information among the plurality of elements of recipe information from the user terminal 10.

In the exemplary embodiment, the recipe providing unit 130 may exclude recipe information including the evasive material information among the plurality of elements of recipe information based on the evasive material information input from the information input unit 110 and provide the user terminal 10 with the recipe information. For example, when a pet has diabetes, a user may input high carbohydrate as the evasive material information through the user terminal 10, and the recipe providing unit 130 may exclude the recipe information including the high carbohydrate among the plurality of elements of recipe information and provide the user terminal 10 with the remaining recipe information.

In another exemplary embodiment, the recipe providing unit 130 may set the evasive material information based on the pet information input from the information input unit 110. For example, when a user does not know exactly which materials should be avoided for a pregnant pet, the user may not input the evasive material information. In order to supplement the problem, when the pet is pregnant, the recipe providing unit 130 may automatically set information about the materials which the pregnant pet should avoid as the evasive material information.

In the exemplary embodiment, the recipe providing unit 130 may select one or more elements of recipe information among the plurality of elements of the recipe information based on the user information and the recipe information which are matched to each other and stored in the storage unit 120, and provide the user terminal 10 which inputs the user information with recommended recipe information. For example, in the case where the user selects often the recipe information in which a protein component is high and a carbohydrate component is low, the recipe providing unit 130 may select the recipe information in which a protein component is high and a carbohydrate component is low among the plurality of elements of the recipe information and provide the user terminal 10 with the selected recipe information as recommended recipe information.

In the exemplary embodiment, the recipe providing unit 130 may provide the user terminal 10 with recipe information including the material information, which is not included in the recipe information selected from the user terminal 10, in the material information including essential nutrients as recommended recipe information.

In the exemplary embodiment, the recipe providing unit 130 may provide one or more elements of recipe information among the plurality of elements of recipe information based on a recipe keyword input from the user terminal 10. For example, a user may input a keyword for a desired recipe through the recipe information search service provided by the system 100 for providing nutritional balance based on pet health information according to the exemplary embodiment of the present invention, and the recipe providing unit 130 may select recipe information corresponding to the input recipe keyword and provide the user terminal 10 with the selected recipe information. However, the present invention is not limited thereto.

The recipe providing unit 130 may determine the amount of recipe supplied included in one or more elements of selected recipe information based on the pet information input from the user terminal 10.

First, the recipe providing unit 130 may calculate the amount of intake requirements of the dry matter according to the pet information based on Equation 1.

$$\text{Amount of intake requirements of dry matter} = \frac{\left(\begin{array}{c}\text{Amount of intake requirements}\\\text{of dry matter according to}\\\text{growth and activity stages} \times\\\text{target weight}^{0.75}\end{array}\right) \times 1000}{\text{Feed energy}}$$

For example, the kind, a breed, growth and activity stages, current weight, and target weight of the pet input from the user terminal 10 may be a dog, schnauzer, a general adult dog, 7 kg, and 7 kg, respectively. The recipe providing unit 130 may obtain data stored in the storage unit 120 based on the input pet information, and it can be known that the amount of intake requirements of the dry matter of the general adult dog is 126 through the obtained data as illustrated in FIG. 7.

The recipe providing unit 130 may calculate the amount of intake requirements of the dry matter by applying the calculated data to Equation 1. In this case, when feed energy is set to 4,000 kcal per 1 kg, it may be calculated as (126*7^0.75)*1000/4000=136, that is, about 136 g.

In the exemplary embodiment, the recipe providing unit 130 may determine the amount of recipe supply based on Equation 2.

$$\text{Amount of recipe supply} = \frac{\left(\begin{array}{c}\text{Amount of intake requirements}\\\text{of dry matter} \times \text{feed energy}\end{array}\right)}{\text{Recipe energy}} \quad <\text{Equation 2}>$$

Herein, the recipe energy may mean the amount of energy that can be dissipated per gram of the recipe selected by the user, and the recipe energy may be calculated based on Equation 3 below.

$$\text{Recipe} = \frac{100\% \text{ dry matter content (recipe)}}{100 \times (100 - \text{moisture feeding state}(\%))} \quad <\text{Equation 3}>$$

Herein, the feeding state (As-Fed) may mean a reference fed to livestock in consideration of the moisture content when a feed component is calculated. For example, when crude protein, crude fat, crude fiber, crude meal, and moisture feeding state (g/kg) included in the recipe information selected by the user are 97.2 g/kg, 82.5 g/kg, 4.4 g/kg, 26.4 g/kg, and 504.1 g/kg, respectively, the feeding state (%) may be 9.7%, 8.3%, 0.4%, 2.6%, and 50.4%, respectively. In this case, the recipe providing unit 130 may calculate a 100% dry matter content based on Equation 4 below.

$$100\% \text{ dry matter content} = 100 \times \frac{\text{Nutrient feeding state}(\%)}{(100 - \text{moisture feeding state }(\%))} \quad <\text{Equation 4}>$$

The 100% dry matter content of the crude protein, the crude fat, the crude fiber, and the crude meal calculated through Equation 4 may be 19.6%, 16.6%, 0.9%, and 0.3%, respectively. The recipe providing unit 130 may calculate a 100% dry matter content of the recipe through the calculated 100% dry matter content. When the 100% dry matter content of the recipe calculated in this process is 4,114.4 g, and is substituted to Equation 3, recipe energy of 2,040.4 kcal may be calculated.

When the recipe providing unit 130 substitutes the recipe energy of 2,040.4 kcal calculated in the foregoing process to Equation 2, the amount of recipe supply of about 266 g, which is (136*4000)/(2,040.4)=266, may be calculated.

In the exemplary embodiment, the recipe providing unit 130 may correct the amount of materials included in the recipe information so as to provide the calculated amount of recipe supply. For example, the amount of recipe supply of the recipe information provided to the user is set based on the provision of 100 g, but when the amount of determined recipe supply is 200 g, the recipe providing unit 130 may correct all of the amounts of materials included in the recipe information by two times and provide the materials to the user.

In the exemplary embodiment, the recipe providing unit 130 may determine whether the user recipe information input from the user terminal 10 is appropriate to be provided to the pet, and may register or delete the user recipe information based on the determination result. For example, the recipe providing unit 130 may compare the amounts of calcium (Ca) and phosphors (P) included in the user recipe information, and determine whether the ratio of Ca/P is 1 to 2.

Calcium and phosphorus are related to each other and affect absorption, and when the ratio of Ca/P is less than 1, the absorption of calcium is disturbed to accompany abnormal endocrine, so that it is highly likely to occur a metabolic disease, such as bone deformation or malformation, and even the case where the ratio of Ca/P is more than 2 corresponds to the case where an optimum ratio of calcium and phosphorus is broken, so that the absorption of calcium may be disturbed. Accordingly, when the ratio of Ca/P is more than 2, the recipe providing unit 130 may delete the user recipe information. However, the present invention is not limited thereto.

In the exemplary embodiment, the system 100 for providing nutritional balance based on pet health information according to the exemplary embodiment of the present invention may further include a sensor unit 140.

The sensor unit 140 may be attached to a body of a pet, and may obtain any one or more among activity information, temperature information, and region information from the pet.

In the exemplary embodiment, the sensor unit 140 may include a GPS sensor 141 and an acceleration sensor 142, and calculate the amount of motion of the pet based on the information sensed by each sensor and correct the amount of recipe supply based on the calculated amount of motion. For example, when the pet has the larger amount of motion than other pets of the same breed, the sensor unit 140 may reflect the larger amount of motion to feed energy and correct a value of the amount of recipe supply.

The sensor unit 140 may include a temperature sensor 143, and may correct a value of the amount of recipe supply according to a temperature of a pet and a temperature of a surrounding environment.

In the exemplary embodiment, the system 100 for providing nutritional balance based on pet health information according to the exemplary embodiment of the present invention may be connected with a material providing system in which a user is capable of buying the materials included in the material information included in the plurality of recipes. Accordingly, the system 100 for providing nutritional balance based on pet health information may provide a user with the plurality of elements of the recipe information and enable the user to immediately buy the materials included in the plurality of elements of the recipe information. Hereinafter, a method of providing a recipe by using the system 100 for providing nutritional balance based on pet health information according to the exemplary embodiment of the present invention will be described with reference to FIG. 16.

FIG. 16 is a flowchart for describing a series of processes for providing a recipe for a pet by using the system 100 for providing nutritional balance based on pet health information according to the exemplary embodiment of the present invention.

First, the system for providing nutritional balance based on pet health information stores the plurality of elements of the recipe information, material information, and the amount of dry matter intake according to the pet information (S110). Herein, the system for providing nutritional balance based on pet health information may receive the corresponding information from an external server and store the received information. However, the present invention is not limited thereto.

Then, a user who desires to receive the recipe information from the system for providing nutritional balance based on pet health information inputs user information and pet information through his/her user terminal (S120).

The system for providing nutritional balance based on pet health information filters the plurality of elements of the pre-stored recipe information based on the user information and the pet information input in operation S120, and provides the filtered recipe information (S130 and S140). Herein, the filtering by the system for providing nutritional balance based on pet health information may mean an operation of excluding specific recipe information among the plurality of elements of the recipe information based on evasive material information input by the user.

The user may receive the recipe information through the user terminal, and select one or more elements of the recipe information among the received recipe information (S150). The system for providing nutritional balance based on pet health information sets the amount of recipe supply of the recipe information selected in operation S150 based on the pet information input in operation S120 (S160). In this case, the system for providing nutritional balance based on pet health information may receive activity information, temperature information, and region information obtained from the sensors attached to the pet, and correct the amount of recipe supply set in operation S160 through the received information (S170 and S180).

The system for providing nutritional balance based on pet health information provides the user with the amount of recipe supply corrected in operation S180 (S190).

As described above, there is an effect in that it is possible to provide the optimum recipe and amount by inputting the pet information, such as the kind, and the growth and activity stages of the pet and the like to the system for providing nutritional balance based on pet health information and determining the amount of recipe supply in consideration of the amount of motion of the pet obtained from the sensor unit, and it is possible to prevent a disease in the pet due to the evasive material by setting the material which the pet should avoid and excluding the recipe including the set evasive material.

The system for providing nutritional balance based on pet health information has been described with reference to the flow chart presented in the drawing. For the simple description, the method is illustrated and described with the series of blocks, but the present invention is not limited to the order of the blocks, and some blocks may occur in the different order from the order illustrated and described in the present specification or may occur with other blocks at the same time, and various other branches, a flow path, and orders of the blocks achieving the same or similar result may be implemented. Further, for the implementation of the method described in the present specification, all of the illustrated blocks may not be required.

In the forgoing, the present invention has been described with reference to the exemplary embodiment of the present invention, but those skilled in the art may appreciate that the present invention may be variously corrected and changed within the range without departing from the spirit and the area of the present invention described in the appending claims.

What is claimed is:

1. A system for providing nutritional balance based on pet health information, the system comprising:
    a nutritional balance providing system including a non-transitory storage unit;
    a sensor unit; and
    a user terminal that is a smart phone configured to communicate with the nutritional balance providing system,
    wherein the nutritional balance providing system is configured to:
    receive pet information from the user terminal;
    provide the user terminal with a plurality of elements of recipe information pre-stored in the non-transitory storage unit of the nutritional balance providing system, and receive a selection of one or more elements of the recipe information among the plurality of elements of recipe information from the user terminal; and
    determine an amount of recipe supply included in the one or more selected elements of recipe information based on the pet information,
    wherein the sensor unit includes a GPS sensor, an acceleration sensor and a temperature sensor, and is configured to be attached to a body of a pet and obtain activity information, temperature information, and region information from the pet,
    wherein the nutritional balance providing system is configured to correct the amount of recipe supply based on the activity information, the temperature information, and the region information, which are obtained by the sensor unit, and
    wherein the nutritional balance providing system is further configured to
    be connected with a material providing system in which a user is capable of buying materials included in material information included in the plurality of elements of the recipe information, and
    provide the user terminal with information on materials, which the user is capable of immediately buying from the material providing system, and
    wherein the user terminal comprises a hair diagnosis kit configured to obtain hair examination information of the pet, and
    the nutritional balance providing system is configured to recognize, based on the obtained hair examination information, nutrition information, which includes information regarding Hg, As, Cd, Pb, Al, Ba, U, Bi, Ni, Ca, Mg, Na, K, Cu, Zn, P, Fe, Mn, Cr and Se of a hair of the pet, and
    adjust a nutritional balance of a recipe based on the nutrition information, and
    wherein the nutritional balance providing system is configured to, when the pet of which a level of Na is measured to be higher than a normal level, adjust a nutritional balance of a recipe to supply of a feed for three weeks with decreased contents of protein, potassium, and calcium of the recipe.

2. The system of claim 1, wherein the pet information includes any one or more among a kind, a breed, growth and activity stages, current weight, target weight, an age, a medical history, pregnancy, spaying or neutering, and evasive material information of a pet.

3. The system of claim 2, wherein the non-transitory storage unit stores any one or more among the plurality of elements of the recipe information, the material information included in the plurality of elements of the recipe information, and an amount of dry matter intake according to the pet information.

4. The system of claim 3, wherein the material information includes any one or more among an origin of a material, classification, a raw material price, a mixing amount, a mixing ratio, a raw material use limit, the amount of dry matters, the amount of moisture, the amount of protein, the amount of fat, the amount of carbohydrate, the amount of tryptophan, the amount of calcium, the amount of phosphorus, the amount of linoleic acid, the amount of ash, the amount of vitamin, the amount of crude fiber, the amount of dietary fiber, the amount of sodium, and the amount of potassium.

5. The system of claim 3, wherein the nutritional balance providing system is further configured to calculate an amount of intake requirements of the dry matter according to the pet information based on Equation 1 below:

<Equation 1>

$$\text{Amount of requirements of dry matter intake} = \frac{\left(\begin{array}{c}\text{Amount of intake requirements}\\ \text{of dry matter according to}\\ \text{growth and activity stages} \times\\ \text{target weight}^{0.75}\end{array}\right) \times 1000}{\text{Feed energy}}.$$

6. The system of claim 5, wherein the nutritional balance providing system is further configured to calculate the amount of recipe supply based on Equation 2 below:

<Equation 2>

$$\text{Amount of recipe supply} = \frac{\left(\begin{array}{c}\text{Amount of intake requirements}\\ \text{of dry matter} \times \text{feed energy}\end{array}\right)}{\text{Recipe energy}}.$$

7. The system of claim 1, wherein the nutritional balance providing system is further configured to exclude recipe information including evasive material information among the plurality of elements of recipe information based on the evasive material information and provide the user terminal with the recipe information.

8. The system of claim 1, wherein the nutritional balance providing system is further configured to receive an input of user information from the user terminal, and the non-transitory storage unit is configured to match the user information and the recipe information selected by the user terminal, and store matching information of the user information and the recipe information.

9. The system of claim 8, wherein the nutritional balance providing system is further configured to provide the user terminal with recommended recipe information based on the matching information.

\* \* \* \* \*